(12) United States Patent
Iwai et al.

(10) Patent No.: US 7,632,633 B2
(45) Date of Patent: Dec. 15, 2009

(54) METHOD FOR DETERMINING THE DEGREE OF PROTEIN OXIDATION IN A SKIN SAMPLE USING OXIDIZED PROTEIN IN STRATUM CORNEUM AS AN INDICATOR

(75) Inventors: Ichiro Iwai, Yokohama (JP); Tetsuji Hirao, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 306 days.

(21) Appl. No.: 10/591,241

(22) PCT Filed: Mar. 4, 2005

(86) PCT No.: PCT/JP2005/004270

§ 371 (c)(1),
(2), (4) Date: Aug. 31, 2006

(87) PCT Pub. No.: WO2005/085844

PCT Pub. Date: Sep. 15, 2005

(65) Prior Publication Data

US 2007/0179198 A1     Aug. 2, 2007

(30) Foreign Application Priority Data

Mar. 5, 2004     (JP) .............................. 2004-062435

(51) Int. Cl.
| G01N 33/50 | (2006.01) |
| G01N 33/483 | (2006.01) |
| G01N 27/00 | (2006.01) |
| C12N 1/00 | (2006.01) |
| G01R 27/00 | (2006.01) |
| G01N 21/64 | (2006.01) |
| G01N 21/75 | (2006.01) |
| A61B 5/00 | (2006.01) |
| A61B 5/05 | (2006.01) |

(52) U.S. Cl. .................. 435/4; 324/692; 435/173.1; 600/306; 600/345; 436/5; 436/63; 436/149; 436/164; 436/172

(58) Field of Classification Search ............... None
See application file for complete search history.

(56) References Cited

U.S. PATENT DOCUMENTS 5,749,847 A * 5/1998 Zewert et al. ............... 604/501

FOREIGN PATENT DOCUMENTS

| EP | 1 354 580 | 10/2003 |
| EP | 1 617 215 | 1/2006 |
| JP | 2001-91514 | 4/2001 |
| JP | 2002-17688 | 1/2002 |
| JP | 2004-340935 | 12/2004 |

OTHER PUBLICATIONS

IBS "Company Profile" retrieved Dec. 4, 2008 from <http://66.102.1.101/translate_c?hl=en&sl=ja&u=http://www.ibs-hama matsu.co.jp/english/company.html&prev=/search%3Fq%3Dibs %2Bhamamatsu%26hl%3Den%26rls%3DGGLD,GGLD:200 4-30, GGLD:en&usg=ALkJrhgdohzfXMZLvw12Zau8k19QBZuiyg>, 2 pages.*
Goldfarb, et al. "The Ultraviolet Absorption Spectra of Proteins", J. Biol. Chem. 1951, 193 (1), pp. 397-404.*
Girard, P. et al. "A New Method for Assessing, in vivo in Human Subjects, the Basal or UV-Induced Peroxidation of the Stratum corneum", Current Problems in Dermatology, 1998, 26, pp. 99-107.*
Iwai, I, et al. "Protein carbonyls damage the water-holding capacity of the stratum corneum" Skin Pharmacol. Physiol. 2008, 21(5), pp. 269-273.*
Richert, S., et al. "Assessment of Skin Carbonyl Content as a Noninvasive Measure of Biological Age" Arch. Biochem. Biophys. 2002, 397(2), pp. 430-432.*
Gillies, R., et al. "Fluorescence Excitation Spectroscopy Provides Information About Human Skin In Vivo" J. Invest. Dermatol. 2000, 115, 704-707.*
Iwai, et al., "The Effect of Oxidative Stress on the Function of Stratum Corneum", *Abstract of the Annual Meeting of Japan Analytical Chemistry Society*, Sep. 1-3, 2004, p. 307, P3085.
Sander, Christina et al., "Photoaging is Associated with Protein Oxidation in Human Skin In Vivo", *The Society for Investigative Dermatology, Inc.*, Apr. 2002, pp. 618-625, vol. 118(4).
Thiele, Jens et al., "Protein Oxidation in Human Stratum Corneum: Susceptibility of Keratins to Oxidation In Vitro and Presence of a Keratin Oxidation Gradient In Vivo", *The Society for Investigative Dermatology, Inc.*, Sep. 1999, pp. 335-359, vol. 113(3).
Iwai, Ichiro et al., "Protein Oxidation Damages the Water-Holding Capacity of the Stratum Corneum", *Free Radical Biology & Medicine*, 2005, p. S124, vol. 39, No. Suppl. 1.
Niwa, Yukie et al., "Protein Oxidative Damage in the Stratum Corneum: Evidence for a Link Between Environmental Oxidants and the Changing Prevalence and Nature of Atopic Dermatitis in Japan", *British Journal of Dermatology*, Aug. 2003, pp. 248-254, vol. 149, No. 2.
Niwa, Yukie et al., "Abnormalities in Serum Lipids and Leukocyte Superoxide Dismutase and Associated Cataract Formation in Patients with Atopic Dermatitis", *Archives of Dermatology*, 1994, pp. 1387-1392, vol. 130, No. 11.
Hashimoto, Kumasaka et al., "In Vitro Comparison of Water-Holding Capacity of the Superficial and Deeper Layers of the Stratum Corneum", *Archives of Dermatological Research*, 1991, pp. 342-346, vol. 283, No. 5.
Thiele, JJ, et al., "Macromolecular carbonyls in human stratum corneum: a biomarker for environmental oxidant exposure?," *FEBS Letters*, Feb. 6, 1998, vol. 422, pp. 403-406.

* cited by examiner

*Primary Examiner*—Christopher R Tate
*Assistant Examiner*—Aaron J Kosar
(74) *Attorney, Agent, or Firm*—Foley & Lardner LLP

(57) ABSTRACT

The present invention provides a method for evaluating the transparency and/or water holding capacity of a stratum corneum by using oxidized protein in the stratum corneum as an indicator.

2 Claims, 5 Drawing Sheets

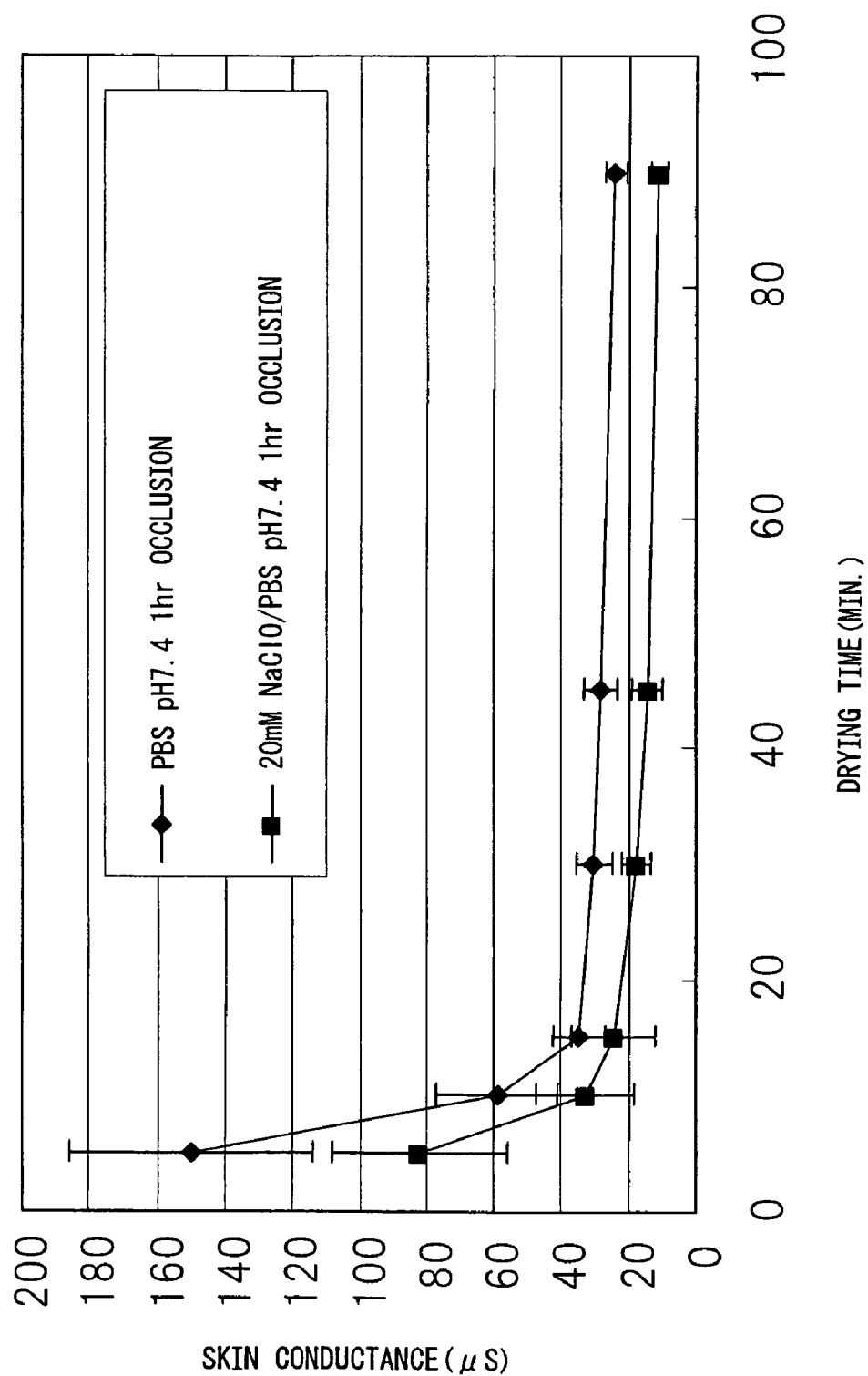

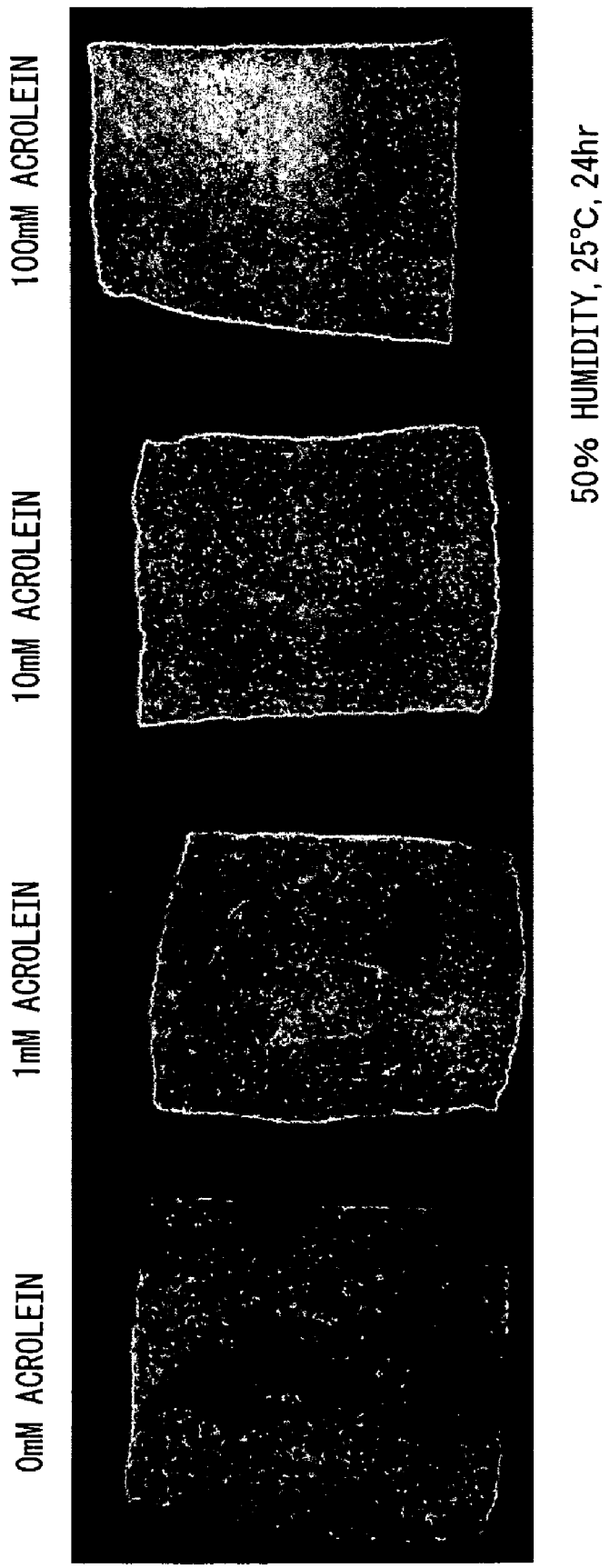

METHOD FOR DETERMINING THE DEGREE OF PROTEIN OXIDATION IN A SKIN SAMPLE USING OXIDIZED PROTEIN IN STRATUM CORNEUM AS AN INDICATOR

TECHNICAL FIELD

The present invention relates to a method for evaluating the transparency and water holding capacity of a stratum corneum using oxidized protein in the stratum corneum as an indicator, a method for detecting the degree of protein oxidation in the stratum corneum using transparency and water holding capacity of the stratum corneum as an indicator, and a method for maintaining and improving transparency and water holding capacity of the stratum corneum by inhibiting oxidation of protein in the stratum corneum.

BACKGROUND ART

Accurate determination of skin type (or skin status) is important in terms of providing effective skin care for maintaining healthy skin. Consequently, when providing skin care using cosmetics, for example, the skin type of a cosmetic user is evaluated through the asking of questions and so forth by a beauty technician. In addition, skin status or function is evaluated according to observed or measured parameters using various types of measuring instruments for the purpose of objectively evaluating skin type.

Research has recently been actively conducted on stratum corneum oxidized proteins in the relationship between aging accompanying aging of the skin and photoaging. Oxidized proteins consist mainly of proteins into which carbonyl groups have been introduced as a result of being subjected to oxidation, and in general, consist of those formed as a result of the $NH_2$ groups of amino acid residues such as Lys, Arg and Pro in proteins being oxidized directly resulting in their conversion to carbonyl groups, and those formed as a result of lipid being oxidized to lipid peroxides, which in turn are degraded into highly reactive aldehydes that bind with protein. As a result of extensive research relating to aging, oxidized proteins are recognized to increase with aging (brain, liver, fibroblasts), in Alzheimer's disease, in progeria (Werner's syndrome), and the like.

In the skin, sebaceous lipid on the skin surface is oxidized by free radicals resulting in the formation of lipid peroxides. The formation of lipid peroxides initializes the oxidation of proteins, and once these lipid peroxides are formed, oxidation proceeds continuously, not only causing irritation on the skin surface, but also penetrating deep into the stratum corneum and damaging cells. Thus, by evaluating the properties of oxidized proteins of the skin, such as the amount present and their distribution state, and determining the skin type or skin status, those evaluation results can be expected to be used in some embodiments for determining the direction of subsequent skin care and selecting cosmetics. At present, however, although there is predicted to be some kind of vague relationship between oxidized proteins and skin damage, the manner in which the oxidation of stratum corneum protein actually affects the properties of the skin has yet to be determined.

DISCLOSURE OF THE INVENTION

If the results of evaluating oxidized proteins present in the skin were able to be used to improve skin type and so forth, it is predicted to be extremely useful in dermatological and cosmetological terms, and for example, would be a useful means for providing counseling services for the purpose of providing advice about suitable skin care methods, which has been performed in the cosmetics industry and so forth in recent years.

As a result of examining the effects of stratum corneum protein on the properties of the skin in consideration of the aforementioned circumstances, the inventors of the present invention found that the water holding capacity and transparency of the stratum corneum are lost as oxidation of stratum corneum protein progresses. Although water holding capacity and transparency are predicted to be lost to a certain extent due to ultraviolet irradiation, drying and aging, the involvement of oxidation of stratum corneum proteins in decreases in water holding capacity and transparency of the stratum corneum is a fact that was discovered for the first time, and the elucidation of this fact is extremely significant from both dermatological and cosmetological standpoints.

Thus, on the basis of elucidation of the aforementioned fact, a first aspect of the present invention provides a method for evaluating the transparency and/or water holding capacity of the stratum corneum by using oxidized protein in the stratum corneum as an indicator. In a preferable aspect thereof, detection of stratum corneum oxidized protein is carried out by specifically and fluorescently labeling carbonyl groups of stratum corneum oxidized protein in a stratum corneum sample collected from the skin, and then detecting the fluorescence thereof. Specific fluorescent labeling of carbonyl groups of oxidized protein is preferably carried out using a hydrazino group-containing fluorescent substance, such as fluoroscein-5-thiosemicarbazide or Texas Red hydrazide, for the oxidized protein.

In another aspect thereof, the present invention provides a method for detecting the degree of oxidation of protein in the stratum corneum by using transparency and/or water holding capacity of the stratum corneum as an indicator.

Moreover, the present invention provides a method for maintaining and improving transparency and/or water holding capacity of the stratum corneum by inhibiting oxidation of protein in the stratum corneum.

Skin care means using stratum corneum oxidized protein as an indicator can be provided by determining the effects of the oxidation of stratum corneum protein on the skin.

BRIEF DESCRIPTION OF THE DRAWINGS

FIG. 4 is a graph showing a decrease in water holding capacity of the stratum corneum of skin of a human arm caused by hypochlorous acid.

FIG. 5 shows a decrease in transparency of the stratum corneum of porcine skin caused by acrolein treatment.

BEST MODE FOR CARRYING OUT THE INVENTION

Figure 1:
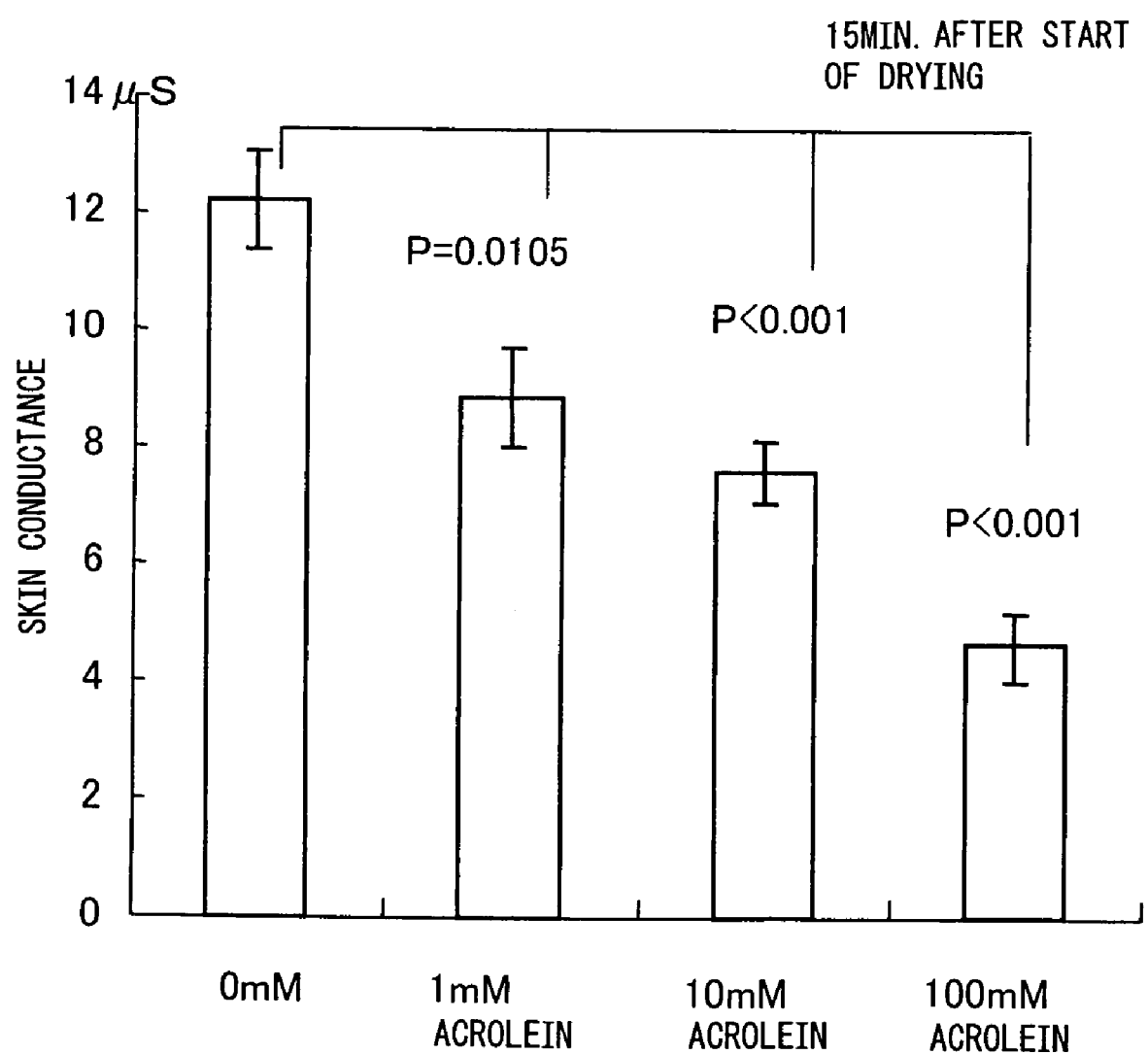
FIG. 1 is a graph showing a decrease in water holding capacity of the stratum corneum of porcine skin caused by acrolein treatment.

In a first aspect thereof, the present invention provides a method for evaluating the transparency and/or water holding capacity of the stratum corneum by using oxidized protein of the stratum corneum as an indicator.

When the "transparency" of the stratum corneum or skin is high, the skin is in a state in which it appears as if you can see through it, and demonstrates an appearance that is aesthetically extremely preferable. In addition, skin having high "water holding capacity" of the stratum corneum or skin is in a healthy state that is youthful and moist. Consequently, it is important aesthetically for the skin to have transparency and moisture retention, and the transparency and water holding capacity of the stratum corneum or skin were typically determined by sensory tests that relied on the subjectivity of a beauty technician or other beauty specialist, or by optical tests and moisture tests on skin samples requiring bothersome procedures or expensive devices and equipment. The present invention makes it possible to investigate the transparency and water holding capacity of the stratum corneum, and even the skin, by a simpler and more objective means by using oxidized protein in the stratum corneum as an indicator, and more specifically, by detecting the amount present and distribution state of oxidized protein in the stratum corneum.

Extensive research has been conducted on stratum corneum oxidized protein, and various methods are known for its detection. In the present invention, there are no particular limitations on the method used to detect stratum corneum oxidized protein, and various methods commonly known in the industry can be used. For example, in the method for detecting stratum corneum oxidized protein described in J. J. Thiele et al., FEBS Letters 1998, Feb. 6, 422(3), 403-406, tape to which the stratum corneum is adhered (stratum corneum-tape) is acquired by carrying out a so-called tape stripping procedure in which adhesive tape is affixed on the skin surface layer and then stripped off, followed by detecting oxidized protein by ELISA. The method described in J. J. Thiele et al., Invest. Dermatol. 1999, September, 113(3), 335-359 detects oxidized protein by extracting protein from a stratum corneum-tape, labeling the soluble components with DNPH, developing by SDS-PAGE, and carrying out Western blotting using anti-DNP antibody. The method described in C. S. Sander et al., J. Invest. Dermatol. 2002, April, 118(4), 618-625 detects oxidized protein by labeling a human skin tissue section with DNPH and staining with anti-DNP.

In a preferable aspect of the present invention, detection of stratum corneum oxidized protein is carried out by specifically and fluorescently labeling carbonyl groups of stratum corneum oxidized protein in a stratum corneum sample collected from the skin, and then detecting the fluorescence thereof. This detection is carried out under a fluorescent microscope. Specific fluorescent labeling of the carbonyl groups of oxidized protein may be preferably carried out by using a hydrazino group-containing fluorescent substance such as fluoroscein-5-thiosemicarbazide or Texas Red hydrazide for the oxidized protein. According to this method, by, for example, generating an image of the detection result obtained by fluorescent microscopy, two-dimensional information on the properties on the skin of oxidized protein of the stratum corneum can be acquired easily, thereby making it possible to, for example, use this oxidized protein information in counseling services in cosmetics sales and so on.

In the present invention, a stratum corneum sample derived from the skin may be a sample derived from any part of the body, or may be cultures of these samples (tissue or cells). Typical examples of parts or regions of the body from which samples are derived include the cheeks or forehead on the face, the back of the hand or the torso.

Although these samples may be acquired by invasive methods such as so-called surgical means and so forth, in the case of using for the purpose of evaluating the type of skin in particular, samples are preferably acquired from the skin by non-invasive methods for reasons of simplicity. Examples of non-invasive methods include tape stripping and rubbing, which are commonly used in the relevant technical field.

Tape stripping is particularly preferable in the present invention since the two-dimensional status of the skin can be transferred directly to adhesive tape by affixing adhesive tape to the surface of the skin and then peeling it off. By collecting a stratum corneum-tape by tape stripping and specifically fluorescently staining oxidized protein while in that state without cutting, two-dimensional information on oxidized protein corresponding to the actual two-dimensional properties of the skin is obtained.

A preferable method for tape stripping consists of first cleaning the surface of the skin with ethanol, for example, to remove any sebaceous lipid and dirt, gently placing a piece of adhesive tape cut to a suitable size (e.g., 5×5 cm) onto the surface of the skin, uniformly applying force to the entire piece of tape to press on flat, and then peeling off the adhesive tape with a uniform force. The adhesive tape may be commercially available cellophane tape, and for example, SCOTCH® SUPER STRENGTH MAILING TAPE (3M) can be used.

In a preferable aspect of the present invention, the fluorescent substance which can be used to specifically and fluorescently label the carbonyl groups of oxidized protein preferably has a hydrazino group ($-NHNH_2$) capable of bonding to the carbonyl groups of oxidized protein. Examples of such fluorescent substances include fluorescein-5-thiosemicarbazide and Texas Red hydrazide.

In the case of using such a hydrazino group-containing fluorescent substance, detection of oxidized protein can be specifically carried out, for example, in the following manner:

(1) a stratum corneum sample is collected by, for example, tape stripping;

(2) this is allowed to react for several hours (for example, 1 hour) at room temperature with a hydrazino group-containing fluorescent substance in a suitable buffer (for example, 100 mM MES-Na buffer (pH 5.5));

(3) following completion of the reaction, oxidized protein is detected with a fluorescent microscope after adequately washing with a suitable physiological solution (for example, phosphate-buffered saline (PBS)); and (4) fluorescent micrography is arbitrarily carried out.

A combination of biotin hydrazide and fluorescent labeled avidin can also be used for the specific fluorescent label of the oxidized protein. Since biotin hydrazide also has a hydrazino group, it is able to bond to carbonyl groups of proteins. In this case, the biotin hydrazide is first bound to the oxidized protein, the fluorescent labeled avidin is subsequently bound to the biotin hydrazide by means of biotin-avidin bonding, and as a result, the oxidized protein is fluorescently labeled. Biotin hydrazide is well known in the art, and the product manufactured and sold by, for example, Pierce Ltd. can be used. In addition, fluorescein avidin and so forth can be used for the fluorescent avidin.

In the case of using such a hydrazino group-containing fluorescent substance, detection of oxidized protein can be specifically carried out, for example, in the following manner:

(1) a stratum corneum sample is collected by, for example, tape stripping;

(2) this is allowed to react for several hours (for example, 1 hour) at room temperature with biotin hydrazide in a suitable buffer (for example, 100 mM MES-Na buffer (pH 5.5));

(3) following completion of the reaction, fluorescent labeled avidin is reacted for several hours (for example, 1 hour) at room temperature after adequately washing with a suitable physiological solution (for example, phosphate-buffered saline (PBS));

(4) the oxidized protein is detected with a fluorescent microscope; and (5) fluorescent micrography is arbitrarily carried out.

Specific fluorescent labeling of oxidized protein can also be carried out by allowing dinitrophenyl hydrazine to act on and bond to carbonyl groups of oxidized protein, followed by labeling the dinitrophenyl portion with a fluorescent dye. Thus, in still another preferable aspect of the present invention, the dinitrophenyl portion of dinitrophenyl hydrazine, which has bonded to the carbonyl groups of oxidized protein, can be detected by fluorescent immunoassay and so forth.

In the case of this fluorescent labeling using dinitrophenyl hydrazine, detection of oxidized protein can be specifically carried out, for example, in the following manner:

(1) a stratum corneum sample is collected by, for example, tape stripping;

(2) this is allowed to react for several hours (for example, 1 hour) at room temperature with dinitrophenyl hydrazine (DNPH) in a suitable buffer (for example, 100 mM MES-Na buffer (pH 5.5));

(3) following completion of the reaction, a suitable physiological solution (for example, phosphate-buffered saline (PBS)) of anti-DNP antibody such as rabbit DNP antibody (Zymed) is reacted for several hours (for example, 1 hour) at room temperature after adequately washing with the same physiological solution;

(4) following completion of this reaction, a fluorescent labeled secondary antibody specific to the aforementioned anti-DNP antibody, such as fluorescein-labeled anti-rabbit Ig (Amersham-Pharmacia-Biotech) is reacted for several hours (for example, 1 hour) at room temperature after adequately washing with the same physiological solution;

(5) the oxidized protein is detected with a fluorescent microscope; and (6) fluorescent micrography is arbitrarily carried out.

In a different aspect thereof, the present invention provides a method for detecting the degree of oxidation of protein in the stratum corneum by using transparency and/or water holding capacity of the stratum corneum as an indicator. As was previously described, although the inventors of the present invention found that oxidation of stratum corneum protein has an effect on the transparency and water holding capacity of skin, oxidation of stratum corneum protein also has the potential for affecting various other properties of the skin, including skin aging. Thus, the present invention is able to allow early detection and treatment of various other properties including skin aging caused by oxidation of stratum corneum protein by using transparency and water holding capacity of the stratum corneum as indicators. As was previously described, transparency and water holding capacity of the stratum corneum and skin can be determined by sensory tests that relied on the subjectivity of a beauty technician or other beauty specialist, or by optical tests and moisture tests on skin samples.

The present invention also provides a method for maintaining transparency and/or water holding capacity of the stratum corneum by inhibiting oxidation of protein in the stratum corneum. Inhibition of oxidation of stratum corneum protein can be achieved by dissolving a suitable antioxidant, such as a commonly known compound such as ascorbic acid or vitamin C, in a suitable solvent followed by applying a suitable amount to the skin.

The following provides a more detailed explanation of the present invention through examples thereof. Furthermore, the present invention is not limited by these examples.

Experiment 1

Evaluation of Stratum Corneum Water Holding Capacity Using Oxidized Protein in Stratum Corneum as an Indicator (1)

Dry pig skin (Alloask, Taiho Pharmaceutical) was immersed in water for 3 days. The pig skin was removed and subjected to oxidation treatment by immersing in an acrolein solution (Tokyo Chemical Industry) at 0, 1, 10 and 100 mM for 3 hours. Acrolein oxidizes by acting on protein resulting in the formation of an aldehyde-protein adduct. Following oxidation treatment, the pig skin was rinsed with water for 1 hour. After rinsing, the pig skin was initially dried (humidity: 50%, temperature: 250° C.) in a Petri dish with the stratum corneum side facing upward followed 15 minutes later by measuring the moisture content of the stratum corneum with the SKINCON-200 (IBS).

The results of measuring the moisture content of the stratum corneum are shown in FIG. 1 as skin conductance values. As is clear from FIG. 1, a decrease in moisture content was observed that was dependent on the concentration of the acrolein used for oxidation treatment. Namely, a decrease was observed in the ability of stratum corneum to hold water as a result of oxidation treatment.

Experiment 2

Evaluation of Stratum Corneum Water Holding Capacity Using Oxidized Protein in Stratum Corneum as an Indicator (2)

Black pig skin was subjected to oxidation treatment for 1 hour with a 10 mM acrolein solution. After rinsing with water for 1 hour, the water was carefully wiped off, and the change in the water content of the stratum corneum over time was measured with the SKINCON-200.

Figure 2:
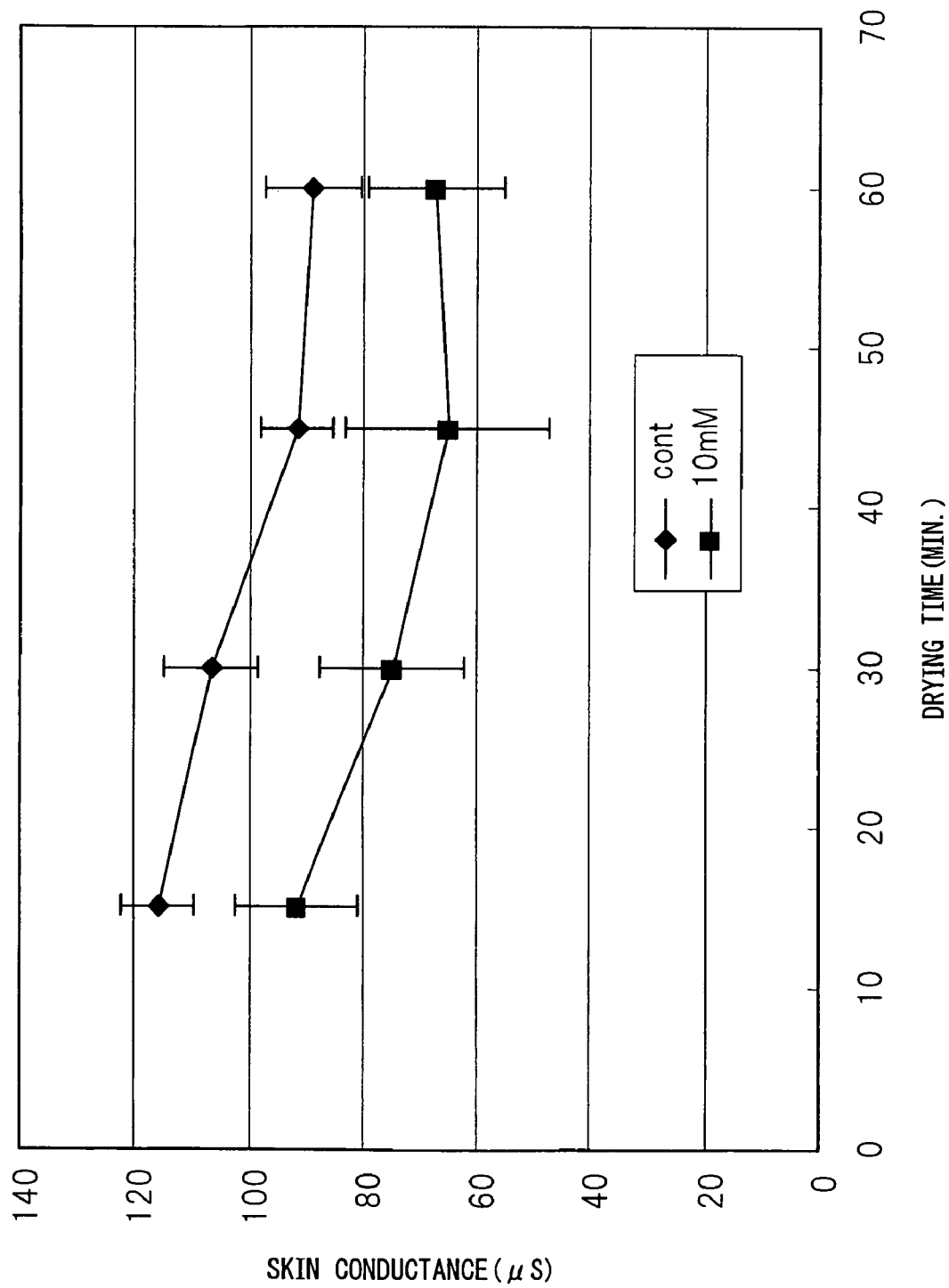
FIG. 2 is a graph showing a decrease in water holding capacity of the stratum corneum of porcine skin caused by acrolein treatment.

Those results are shown in FIG. 2. A decrease was observed in the ability of stratum corneum of the pig skin to hold water as a result of oxidation treatment with acrolein.

Experiment 3

Evaluation of Stratum Corneum Water Holding Capacity Using Oxidized Protein in Stratum Corneum as an Indicator (3)

Black pig skin was treated for 1 hour with 20 mM hypochlorous acid. After rinsing with water for 1 hour, the water was carefully wiped off, and the change in the water content of the stratum corneum over time was measured with the SKINCON-200.

Figure 3:
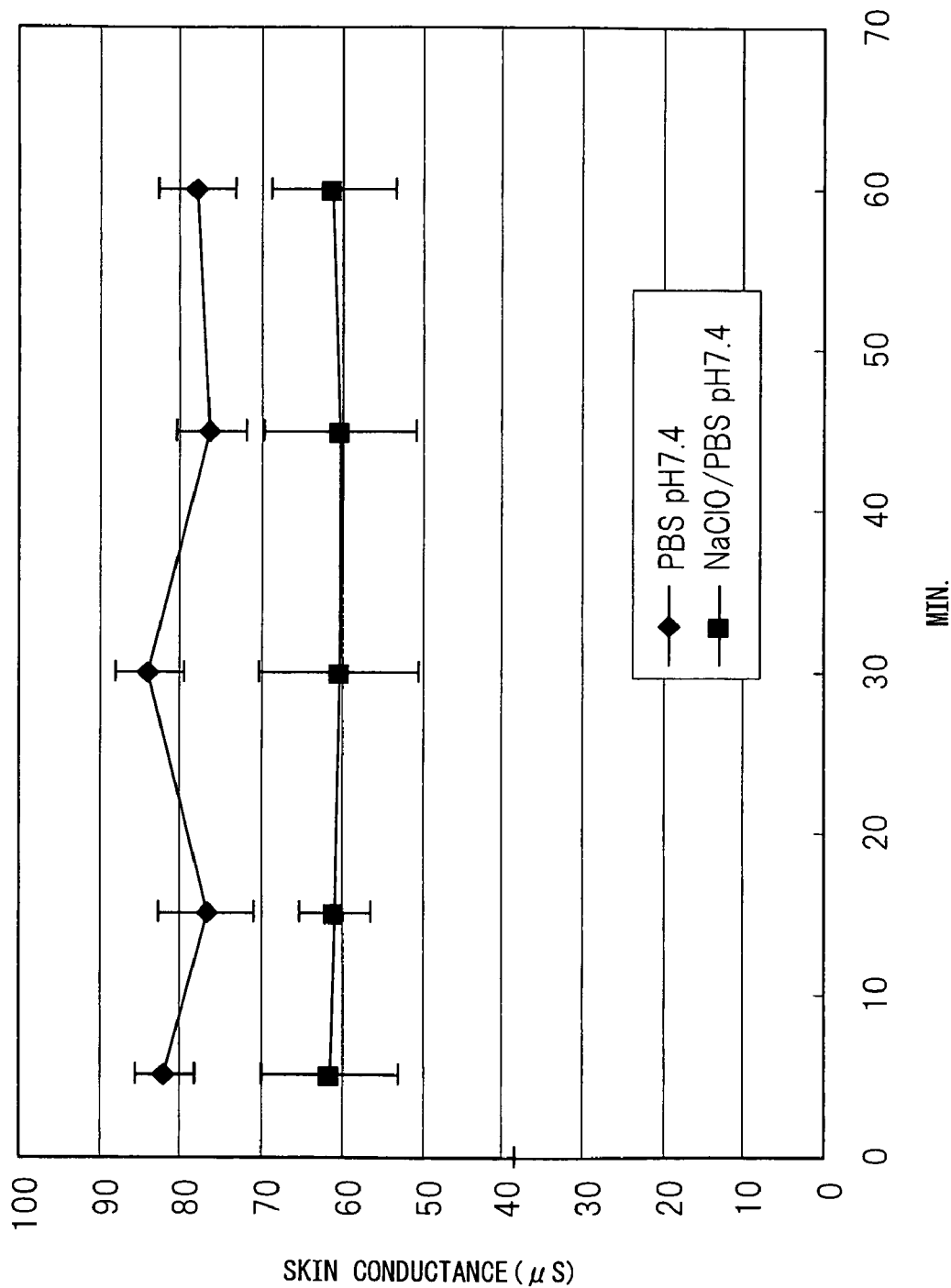
FIG. 3 is a graph showing a decrease in water holding capacity of the stratum corneum of porcine skin caused by hypochlorous acid (20 mM, 1 hr).

Those results are shown in FIG. 3. A decrease was observed in the ability of stratum corneum of the pig skin to hold water as a result of oxidation treatment with hypochlorous acid.

Experiment 4

Evaluation of Stratum Corneum Water Holding Capacity Using Oxidized Protein in Stratum Corneum as an Indicator (4)

Human forearm skin was subjected to occlusion treatment for 1 hour with PBS or 20 mM hypochlorous acid. After rinsing with water for 1 hour, the water was carefully wiped off, and the change in the water content of the stratum corneum over time was measured with the SKINCON-200.

Those results are shown in FIG. 4. A decrease was observed in the ability of stratum corneum of the human skin as well to retain moisture as a result of oxidation treatment.

Experiment 5

Evaluation of Stratum Corneum Transparency Using Oxidized Protein in Stratum Corneum as an Indicator Dry pig skin (Alloask, Taiho Pharmaceutical) was immersed in water for 3 days. The pig skin was subjected to oxidation treatment by immersing in an acrolein solution (Tokyo Chemical Industry) at 0, 1, 10 and 100 mM for 3 hours. Acrolein oxidizes by acting on protein resulting in the formation of an aldehyde-protein adduct. Following oxidation treatment, the pig skin was rinsed with water for 1 hour. After rinsing, the pig skin was initially dried (humidity: 50%, temperature: 25° C.) in a Petri dish with the stratum corneum side facing upward followed by observation of the dried pig skin over the course of 24 hours.

Those results are shown in FIG. 5. As is clear from FIG. 5, in contrast to the transparency of pig skin not subjected to oxidation treatment being high, transparency decreased concentration-dependently when treated with acrolein.

The invention claimed is:

1. A method of determining the degree of protein oxidation in a skin sample comprising stratum corneum, the method comprising:
(a) providing a skin sample (S) selected from the group comprising:
  (i) stratum corneum having carbonylated protein; or
  (ii) oxidized stratum corneum, wherein the oxidized stratum corneum is obtained by contacting a skin sample comprising stratum corneum with an oxidizing agent and wherein the oxidizing agent comprises acrolein, thereby forming an acrolein-protein adduct;
wherein the skin sample (S) comprising said stratum corneum (i) or said oxidized stratum corneum (ii) is contacted and fluorescently labeled with a hydrazine fluorophore, the hydrazine fluorophore selected from the group consisting of fluorescein-thiosemicarbazide; Texas Red hydrazide; biotin hydrazide reacted with fluorescein avidin; dintrophenylhydrazine (DNPH) reacted with anti-DNP antibody and with a fluorescein-labeled secondary antibody specific to the anti-DNP antibody; and DNPH reacted with a fluorescent dye;
(b) measuring the fluorescence of the skin sample (S); and then
(c) determining the degree of protein oxidation of the skin sample (S),
  (i) wherein the fluorescence intensity of the skin sample (S) is indicative of the degree of protein oxidation in the skin sample (S);
  (ii) wherein, relative to the fluorescence intensity of a skin sample not treated with acrolein (S'), an increased fluorescence intensity of the skin sample (S) indicates an increased protein oxidation in the skin sample (S); and
  (iii) wherein said skin sample (S) has increased protein oxidation.

2. The method of claim 1, further comprising:
(d) measuring the conductance of a skin sample (S") comprising stratum corneum, wherein the skin sample (S") is oxidized by contacting with an oxidizing agent, wherein said oxidizing agent is selected from the group consisting of hypochlorous acid and acrolein, and wherein an increase in protein oxidation provides a decrease in conductance of the skin sample (S") relative to the conductance of a skin sample not contacted with an oxidizing agent (S').

* * * * *